(12) United States Patent
Golik et al.

(10) Patent No.: US 6,235,728 B1
(45) Date of Patent: May 22, 2001

(54) WATER-SOLUBLE PRODRUGS OF AZOLE COMPOUNDS

(75) Inventors: Jerzy Golik, Southington; John D. Matiskella, Wallingford; Yasutsugu Ueda, Clinton, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/503,616

(22) Filed: Feb. 11, 2000

Related U.S. Application Data

(60) Provisional application No. 60/124,397, filed on Mar. 15, 1999, and provisional application No. 60/120,954, filed on Feb. 19, 1999.

(51) Int. Cl.⁷ .............................. A61K 31/675; C07F 9/06
(52) U.S. Cl. .............................................. 514/93; 548/112
(58) Field of Search ................................. 548/112; 514/93

(56) References Cited

U.S. PATENT DOCUMENTS

| | | | |
|---|---|---|---|
| 4,291,047 | * 9/1981 | Kranz et al. | 424/273 |
| 4,535,074 | * 8/1985 | Preuss et al. | 514/93 |
| 5,648,372 | 7/1997 | Toshihiko et al. | |
| 5,985,856 | 11/1999 | Stella et al. | |

FOREIGN PATENT DOCUMENTS

| | | |
|---|---|---|
| 829478A2 | 3/1998 | (EP) . |
| WO 97/28169 | 8/1997 | (WO) . |
| WO 98/43970 | 10/1998 | (WO) . |

OTHER PUBLICATIONS

Z. Zwierzak and M. Kluba, Tetrahedron, 27, pp. 3163–3170, 1971.

* cited by examiner

*Primary Examiner*—Deborah C. Lambkin
*Assistant Examiner*—Sonya N. Wright
(74) *Attorney, Agent, or Firm*—David M. Morse

(57) ABSTRACT

Water soluble prodrugs of azole antifungal agents are provided by quaternizing a nitrogen atom of the azole ring with a phosphonooxymethyl group.

6 Claims, No Drawings

WATER-SOLUBLE PRODRUGS OF AZOLE COMPOUNDS

This application claims the benefit of U.S. Provisional 60/124,397 filed Mar. 15, 1999 which claims the benefit of U.S. Provisional 60/120,954 filed Feb. 19, 1999.

BACKGROUND OF THE INVENTION

1. Field of the Invention

This invention relates to novel water-soluble azole compounds useful for the treatment of serious systemic fungal infections and suitable for both oral and, particularly, parenteral administration. More particularly, the invention relates to novel water-soluble prodrugs having the general formula

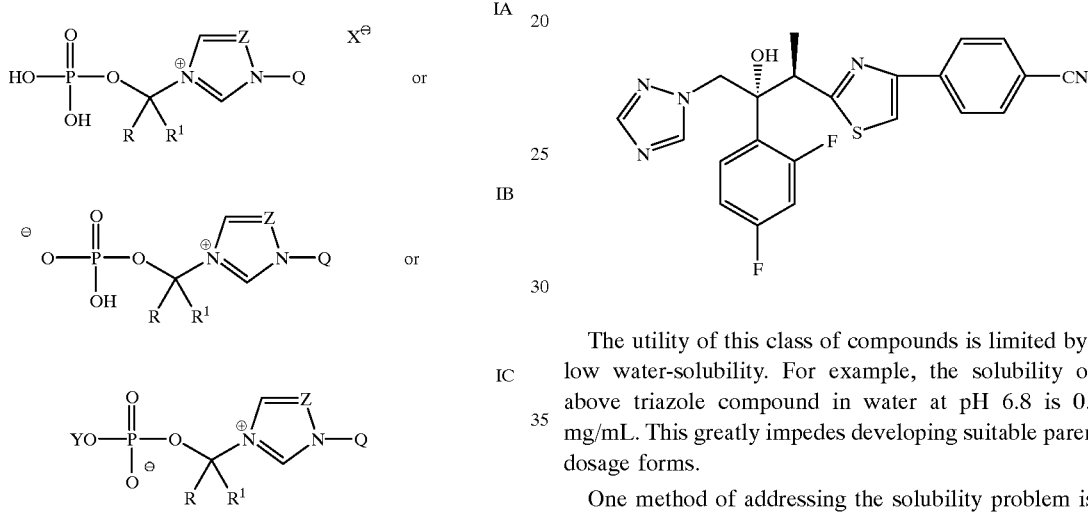

wherein R and $R^1$ are each independently hydrogen or $(C_1-C_6)$alkyl, Z is nitrogen or CH, Q is the residue of an azole compound of the formula

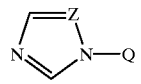

possessing antifungal activity, $X^\ominus$ is a pharmaceutically acceptable anion and Y is a pharmaceutically acceptable cation.

2. Description of the Prior Art

Azole antifungal compounds are well-known in the prior art. U.S. Pat. No. 5,648,372 discloses that (2R,3R)-3-[4-(4-cyanophenyl)thiazol-2-yl]-2-(2,4-difluorophenyl)-1-(1H,1,2,4-triazol-1-yl)-butan-2-ol has potent antifungal activity.

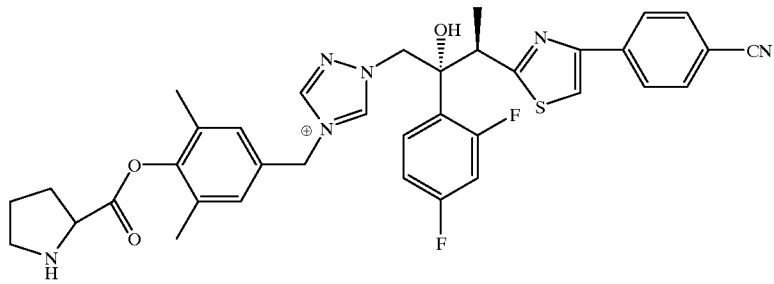

The utility of this class of compounds is limited by their low water-solubility. For example, the solubility of the above triazole compound in water at pH 6.8 is 0.0006 mg/mL. This greatly impedes developing suitable parenteral dosage forms.

One method of addressing the solubility problem is disclosed in European Published Application 829,478 where the water-solubility of an azole antifungal agent was increased by attaching a linked amino-acid to the azole portion of the molecule.

Alternatively, WO 97/28169 discloses that a phosphate moiety can be attached directly to the tertiary hydroxyl portion of the anti-fungal compound, e.g. the compound having the formula

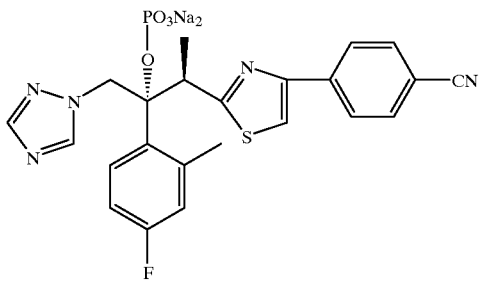

Published European Patent Application 829,478 discloses water-soluble azole compounds of the general formula

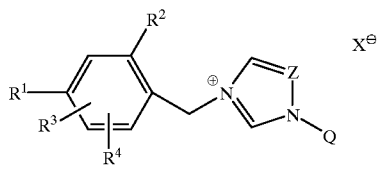

wherein
Q is the remainder of an azole compound of the formula

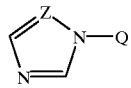

possessing antifungal activity;
Z is nitrogen or methine;
$R^1$ and $R^2$ are each independently hydrogen or —OY in which Y is an easily hydrolyzable ester;
$R^3$ and $R^4$ are each independently a hydrogen or halogen atom, lower alkyl, lower alkoxy, lower alkylthio, (lower-alkylcarbonyl)thiomethyl, carboxy or methoxycarbonyl; and $X^{\ominus}$ is a pharmaceutically acceptable anion.

Published PCT Application WO 98/43970 discloses quaternized nitrogen-containing imidazol-1-yl or 1,2,4-triazol-1-yl compounds where one of the nitrogen atoms constituting an azole ring is quaternized with a substituent capable of being eliminated in vivo and the substituent can be eliminated in vivo to be converted into an azole antifungal compound. Specifically disclosed are prodrugs wherein the nitrogen atom of the azole ring is quaternized by a group of the formula

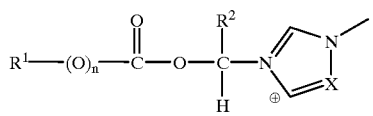

wherein $R^1$ is an optionally substituted hydrocarbon group or an optionally substituted heterocyclic group; $R^2$ is a hydrogen atom or a lower alkyl group; X is a nitrogen atom or a methine group; and n is 0 or 1.

SUMMARY OF THE INVENTION

The present invention provides water-soluble azole antifungal agents of the formula

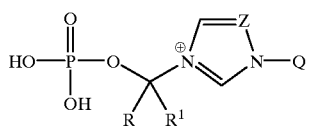

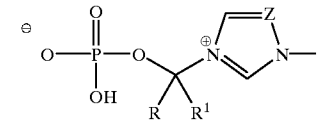

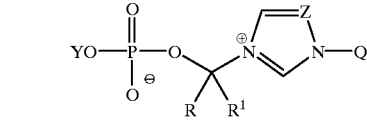

wherein R and $R^1$ are each independently hydrogen or $(C_1-C_6)$alkyl, Z is nitrogen or CH, Q is the residue of an azole compound of the formula

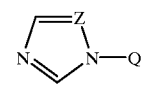

possessing antifungal activity, $X^{\ominus}$ is a pharmaceutically acceptable anion and Y is a pharmaceutically acceptable cation.

The compounds of general formula IA, IB and IC function as "prodrugs" when administered in vivo, being converted to the biologically active parent azole in the presence of alkaline phosphatase.

Preferred among the compounds of formula I are those wherein R and $R^1$ are both hydrogen.

DETAILED DESCRIPTION OF THE INVENTION

As used herein "$(C_1-C_6)$alkyl" refers to a straight or branched chain saturated aliphatic hydrocarbon group having 1 to 6 carbon atoms such as methyl, ethyl, n-propyl, isopropyl, n-butyl, sec-butyl, t-butyl, n-pentyl, etc.

An anion represented by $X^{\ominus}$ is derived from a pharmaceutically acceptable organic or inorganic acid, e.g. inorganic acids such as hydrochloric, sulfuric, phosphoric, hydrofluoric, hydrobromic, hydroiodic, etc. or aliphatic, aromatic or araliphatic organic acids such as acetic, propionic, methanesulfonic, benzenesulfonic, maleic, citric, succinic, fumaric, mandelic, ascorbic, lactic, gluconic, toluenesulfonic, trifluoromethanesulfonic, trifluoroacetic, etc. Such compounds are also referred to as "pharmaceutically acceptable salts."

The "Y" substituent shown in structure IC above is a pharmaceutically acceptable cation such as ammonium, an alkali metal (e.g. Na, K, Li, etc.), an alkaline earth metal (e.g. Ca, Mg) or salts with suitable organic bases such as (lower) alkylamines (methylamine, ethylamine, cyclohexylamine, and the like) or with substituted (lower) alkylamines, e.g. hydroxyl-substituted alkylamines such as diethanolamine, triethanolamine or tris(hydroxymethyl)-aminomethane), or with bases such as piperidine or morphiline.

The compounds of the present invention can be solvated or non-solvated. A preferred solvate is a hydrate.

Substituent "Z" in the azole ring may be nitrogen, e.g.

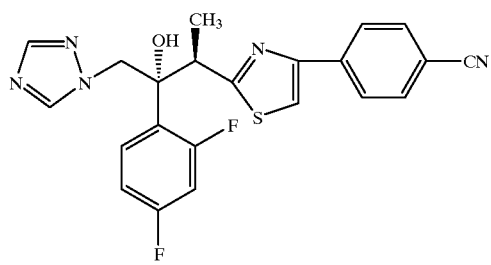

or CH, e.g.

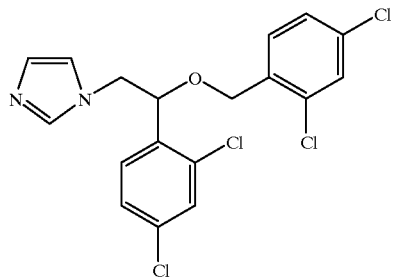

The azole of formula II can be a wide variety of azole antifungal agents, including known azole antifungal agents such as miconazole, ketoconazole, fluconazole, itraconazole, saperconazole, clotrimazole, econazole, isoconazole, sulconazole, butoconazole, tioconazole, fenticonazole, omoconazole, flutrimazole, eberconazole, lanoconazole, neticonazole, sertaconazole, genaconazole, Sch-56592, Sch-51048, VR-9746, MFB-1041, VR-9751, T-8581, VR-9825, SSY-726, D-0870, KP-103, ER-30346, etc. The azole compounds, however, are not limited to known antifungal agents and any azole compound of formula II possessing clinically useful antifungal activity is suitable for use in the present invention. The azoles having optical centers may be employed in the form of racemic mixtures or individual separated enantiomers.

A preferred group of compounds I are those wherein Z is nitrogen and Q is

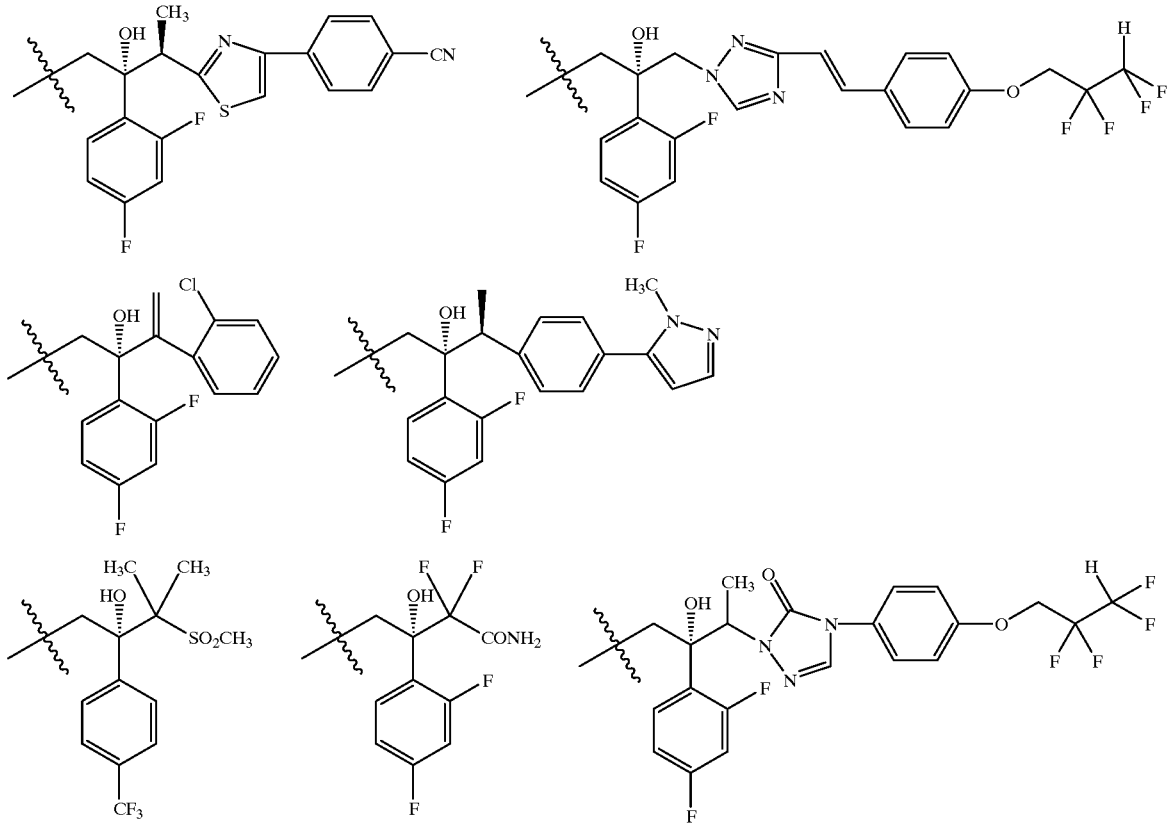

-continued
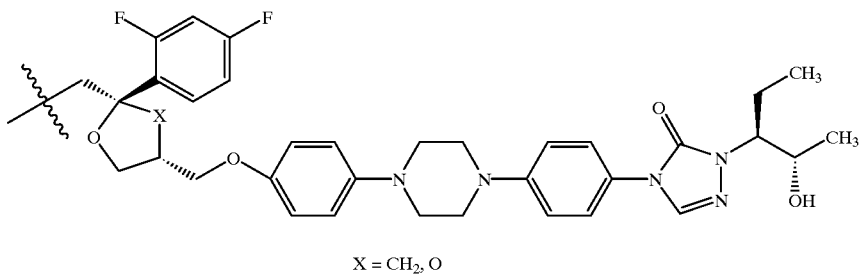
X = CH₂, O
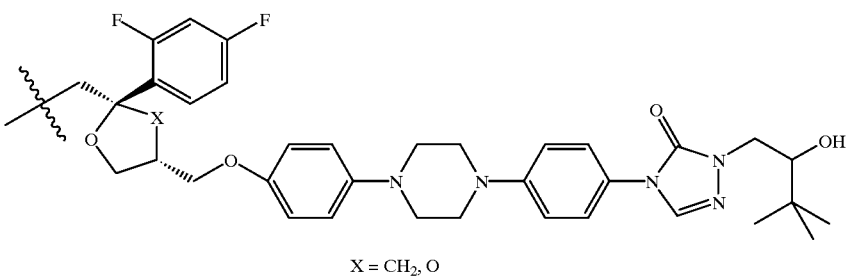
X = CH₂, O
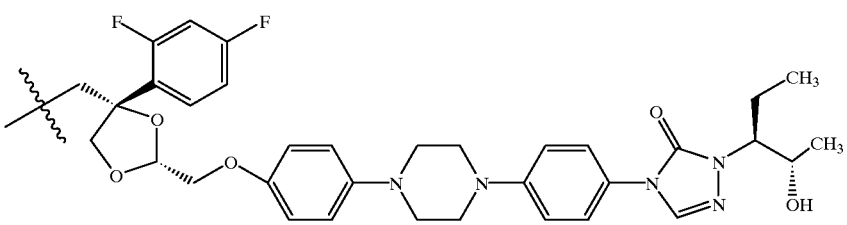
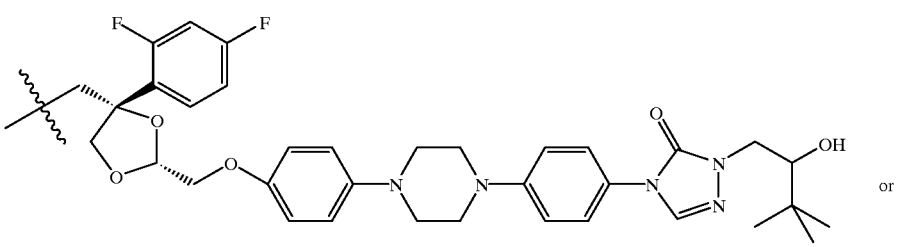
or
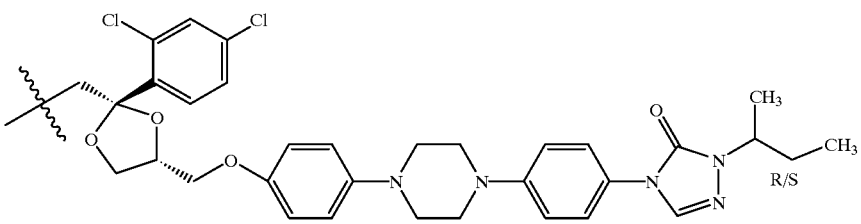
(also its racemate as in itraconazole)

Another preferred group of azole antifungal agents II for use in preparing compounds I are those wherein Z is CH and Q represents

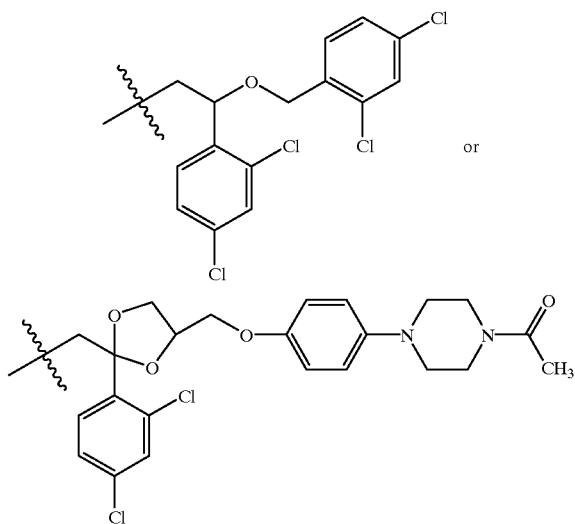

or

Compounds where R and R¹ are both hydrogen are most preferred in the above-mentioned two groups.

A preferred azole antifungal agent II is itraconazole.

An especially preferred azole antifungal agent II is (2R,3R)-3-[4-(4-cyanophenyl)thiazol-2-yl]-2-(2,4-difluorophenyl)-1-(1H,1,2,4-triazol-1-yl)-butan-2-ol described in U.S. Pat. No. 5,648,372 and having the structural formula

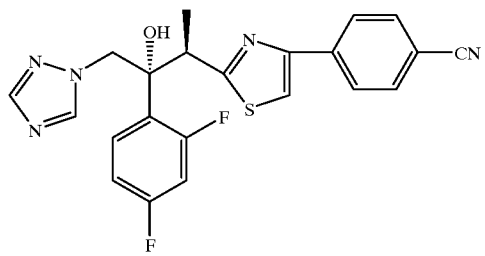

Compounds I prepared from this azole, especially the compounds where R and R¹ are both hydrogen, exhibit much improved aqueous solubility (>1 mg/ml) over the parent triazole which enables them to be useful for parenteral administration as well as oral administration. Also, these compounds are stable in solution, can be isolated in crystalline form and are readily converted to parent drug in vivo.

The compounds of the present invention can be prepared according to the procedures illustrated below. In general, the triazole antifungal agent of the formula

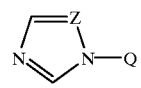

II wherein Z is nitrogen or CH and Q is the residue of an azole compound having antifungal activity is quaternized with a reagent of the formula

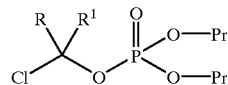

III in which R and R¹ are as defined above and Pr represents a hydroxyl protecting group such as t-butyl, benzyl or allyl in the presence or absence of an organic solvent such as tetrahydrofuran, acetonitrile or acetone at a temperature above about 75° C. to form

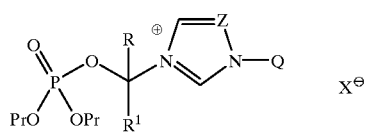

IV in which Q, Z, X$^\ominus$, R, R¹ and Pr are as defined above, followed by removal of the hydroxyl protecting groups to give compound IA.

The quaternization may be achieved in the absence or in the presence of other aprotic solvents such as dimethylformaldehyde, dimethylacetaldehyde and N-methylpyrrolidinone at an elevated temperature of above about 75° C. When a separate solvent is employed the solvent may be slowly evaporated with a stream of anhydrous nitrogen to form IV.

The most preferred hydroxy protecting group is the t-butyl group, in which case, the t-butyl group is removed during the quaternization process.

The preferred organic solvent is tetrahydrofuran and the preferred bath temperature range is from about 75° C. to 85° C.

The so-obtained compound may be thereafter converted to a compound having a different anion X$^\ominus$, e.g. by anion exchange, or converted to a desirable pharmaceutically acceptable solvate, e.g. hydrate.

Zwitterionic form IB may be prepared from salt form IA by use of column chromatography e.g. using reverse phase $C_{18}$ silica gel, eluting with acetonitrile-water, followed by crystallization from water.

The compound in form IC may be prepared from the salt form IA by basification followed by column chromatography, e.g. using reverse phase $C_{18}$ silica gel, eluting with acetonitrile-water.

The compounds of the present invention may be used alone or formulated as pharmaceutical compositions comprising, in addition to the active triazole ingredient, a pharmaceutically acceptable carrier, adjuvant or diluent. The compounds may be administered by a variety of means, for example, parenterally (intravenous or intramuscular injection), orally or topically. The pharmaceutical compositions may be in solid form such as capsules, tablets, powders, etc. or in liquid form such as solutions, suspensions or emulsions. Compositions for injection may be prepared in unit dose form in ampules or in multidose containers and may contain additives such as suspending, stabilizing and dispersing agents. The compositions may be in ready-to-use form or in powder form for reconstitution at the time of delivery with a suitable vehicle such as sterile water.

Alternatively, the compounds of the present invention can be administered in the form of a suppository or pessary, or they may be applied topically in the form of a lotion, solution, or cream. Additionally, they may be incorporated (at a concentration up to 10%) into an ointment consisting of a white wax or soft, white paraffin base together with the required stabilizers and/or preservatives.

The compounds of the invention are useful because they possess pharmacological activities in animals, including particularly mammals and most particularly, humans. Specifically, the compounds of the present invention are useful for the treatment of systemic fungal infections caused, for example, by species of Candida such as *Candida albicans, Cryptococcus neoformans, Aspergillus flavus, Aspergillus fumigatus*, Coccidioides, Paracoccidiodes, Histoplasma, or Blastomyces, for the treatment of mucosal infections caused by *Candida albicans*, and for the treatment or prevention of topical fungal infections, including those caused by species of Candida, Trichophyton, Microsporum, or Epidermophyton.

Thus, according to another aspect of the invention, there is provided a method of treating a fungal infection which comprises administering a therapeutically effective amount of a compound of the present invention to a host, particularly a mammalian host and most particularly a human patient. The use of the compounds of the present invention as pharmaceuticals and the use of the compounds of the invention in the manufacture of a medicament for the treatment of fungal infections are also provided.

The dosage to be administered depends, to a large extent, on the particular compound being used, the particular composition formulated, the route of administration, the nature and condition of the host and the particular situs and organism being treated. Selection of the particular preferred dosage and route of application, then, is left to the discretion of the physician or veterinarian. In general, however, the compounds may be administered parenterally or orally to mammalian hosts in an amount of from about 5 mg/day to about 1.0 g/day. These doses are exemplary of the average case, and there can be individual instances where higher or lower dosages are merited, and such dosages are within the scope of this invention. Furthermore, administration of the compounds of the present inventions can be conducted in either single or divided doses.

The in vitro evaluation of the antifungal activities of the compounds of the invention can be performed by determining the minimum inhibitory concentration (MIC). The MIC is the concentration of test compound which inhibits the growth of the test microorganism. In practice, a series of agar plates, each having the test compound incorporated at a specific concentration, is inoculated with a fungal strain and each plate is then incubated for 48 h at 37° C. The plates are examined for the presence or absence of fungal growth, and the relevant concentration is noted. Microorganisms which can be used in the test include *Candida albicans, Asperigillus fumigatus*, Trichophyton spp., Microsporum spp., *Epidermophyton floccosum, Coccidioides immitis*, and *Torulopsos galbrata*. It should be recognized that, as prodrugs, some compounds of the invention may not be active in the in vitro test.

The in vivo evaluation of compounds of the present invention can be carried out at a series of dose levels by intraperitoneal, subcutaneous or intravenous injection or by oral administration to mice which have been inoculated with a strain of fungus (e.g. *Candida albicans*). Activity is determined by comparing the survival of the treated group of mice at different dosage levels after the death of an untreated group of mice. The dose level at which the test compound provides 50% protection against the lethal effect of the infection is noted.

The compounds of the present invention substantially increase the solubility of the parent triazole antifungal compound and also release the bioactive parent compound (i.e. function as a prodrug) in both rat and human liver homogenates (S 9 preparations).

ILLUSTRATIVE EXAMPLE

The following examples illustrate the invention, but are not intended as a limitation thereof.

In the examples, all temperatures are given in degrees Centigrade. Melting points were determined on an electrothermal apparatus and are not corrected. Proton nuclear magnetic resonance ($^1$H NMR) spectra were recorded on a Bruker DPX-300, AM-300, DRX-500, AM-500 or a Varian Gemini 300 spectrometer. Fluorine nuclear magnetic resonance ($^{19}$F NMR) spectra were recorded on a Bruker DPX-300 spectrometer using trifluoroacetic acid as an external reference (δ −76.0 ppm). All spectra were determined in CDCl$_3$, DMSO-d$_6$, CD$_3$OD, or D$_2$O unless otherwise indicated. Chemical shifts are reported in δ units relative to tetramethylsilane (TMS) or a reference solvent peak and interproton coupling constants are reported in Hertz (Hz). Splitting patterns are designated as follows: s, singlet; d, doublet; t, triplet; q, quartet; m, multiplet; br, broad peak; dd, doublet of doublets; dt, doublet of triplets; and app d, apparent doublet, etc. Mass spectra were recorded on a Kratos MS-50 or a Finnegan 4500 instrument utilizing direct chemical ionization (DCI, isobutene), fast atom bombardment (FAB), or electron spray ionization (ESI).

Example 1

(2R,3R)-3-[4-(4-cyanophenyl)thiazol-2-yl]-2-(2,4-difluorophenyl)-1-(1H, 4-phosphonooxymethyl-1,2,4-triazol-1-yl)butan-2-ol

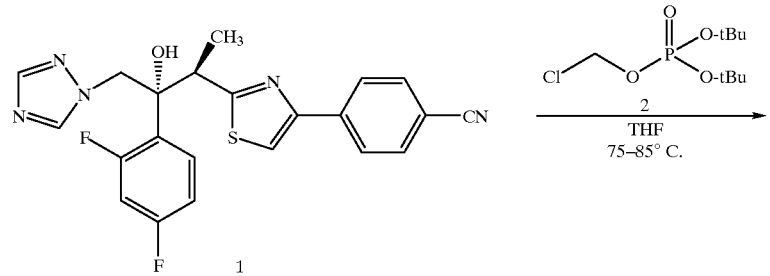

-continued

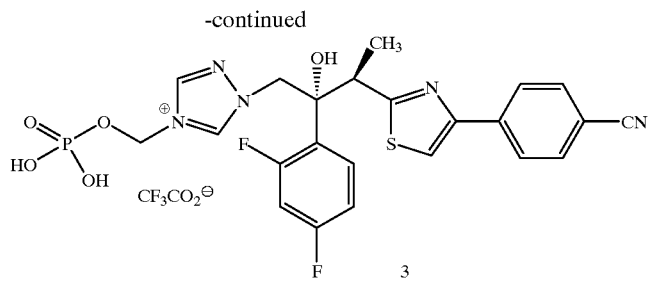

3

To a suspension of (2R,3R)-3-[4-(4-cyanophenyl)thiazol-2-yl]-2-(2,4-difluorophenyl)-1-(1H-1,2,4-triazol-1-yl)butan-2-ol, 1 (2.17 g, 5 mmol) in THF (5 mL) was added di-tert-butyl chloromethyl phosphate 2 (2.58 g, 10 mmol). The mixture was heated at 75° C. in an oil bath with stirring under stream of anhydrous nitrogen. The THF was slowly evaporated during 5–6 hrs period. After 18 hrs, the viscous reaction mixture was heated at 85° C. for another 20 hrs. After cooling, this crude thick oil was dissolved in a minimum amount of 25% acetonitrile-water containing 10 mmol of trifluoroacetic acid (TFA) and chromatographed on reverse phase $C_{18}$ silica using 25% acetonitrile-water containing 0.1% TFA as an eluent. The concentration of acetonitrile was raised up to 35% as the chromatography progressed. Pure fractions were concentrated, frozen and lyophilized to give the title compound 3 (1.4 g, 2.12 mmol, 42% yield) as a white fluffy powder: $^1$H NMR (DMSO-d6): δ 10.12 (s, 1H), 9.02 (s, 1H), 8.45 (s, 1H), 8.20 (d, 2H, J=9), 7.93 (d, 2H, J=9), 7.36–7.25 (m, 2H), 7.01–6.94 (m, 1H), 5.93–5.72 (m, 2H), 5.04 (d, 1H, J=14), 4.77 (d, 1H, J=14), 4.01 (q, 1H, J=7), 1.16 (d, 3H, J=7); MS (MH$^+$=548); $^{19}$F NMR (DMSO-d6): d −74.55 (s, 4F), −107.5 (s, 1F), −111.1 (s, 1F); Anal. Calcd for $C_{23}H_{20}F_2N_5O_5SP/1.5CF_3CO_2H/0.5H_2O$: C 42.92, H 3.12, N 9.63, F 16.97, $H_2O$ 1.30. Found: C 43.38, H3.13, N 9.60, F 17.21, $H_2O$ 1.12 (Karl Fischer Method).

The sodium salt of the title compound was prepared as amorphous powder from the trifluoroacetate salt by basification with sodium hydroxide followed by column chromatography on reverse phase $C_{18}$ silica gel, eluting with acetonitrile-water.

Preparation of di-tert-butyl chloromethyl phosphate, 2:

Silver di-t-butyl phosphate (6.34 g, 20 mmol), which was prepared by mixing di-t-butyl phosphate (obtained from di-t-butyl phosphite by the method of Zwierzak and Kluba, Tetrahedron, 1971, 27, 3163) with one equivalent of silver carbonate in 50% aqueous acetonitrile and by lyophilizing to dryness, was placed together with chloroiodomethane (35 g, 200 mmol) in benzene and stirred at room temperature for 18 hrs. The reaction mixture was filtered and the filtrate concentrated under reduced pressure. The residue was chromatographed on silica and eluted with 2:1 hexanes-ethyl acetate. Appropriate fractions were concentrated to dryness to obtain the subtitle compound 2 (3.7 g, 71% yield): $^1$H NMR (CDCl$_3$) δ 5.63 (d, 2H, J=17), 1.51 (s, 18H); MS (MH$^+$=259).

Example 2

Preparation of N-phosphonooxymethyl itraconazole

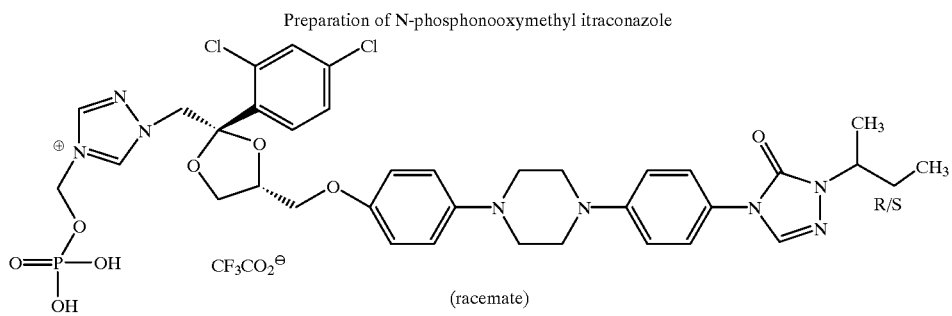

(racemate)

The zwitterionic form of the title compound was prepared as white crystals from the trifluoroacetate salt by column chromatography on reverse phase $C_{18}$ silica gel, eluting with 30% acetonitrile-water as an eluent, followed by crystallization from water: mp 145–155° C.; $^1$H NMR (DMSO-d6): δ 10.21 (s, 1H), 8.98 (s, 1H), 8.39 (s, 1H), 8.17 (d, 2H, J=9), 7.90 (d, 2H, J=9), 7.38–7.25 (m, 2H), 6.97–6.91 (m, 1H), 5.76–5.60 (m, 2H), 5.00 (d, 1H, J=14), 4.75 (d, 1H, J=14), 4.04 (q, 1H, J=7), 1.16 (d, 3H, J=7); MS (MH$^+$=548); $^{19}$F NMR (DMSO-d6): δ −73.87 (s, 0.1F), −107.5 (s, 1F), −111.3 (s, 1F); Anal. Calcd for $C_{23}H_{20}F_2N_5O_5SP/0.05CF_3CO_2H/0.4H_2O$: C 49.51, H 3.75, N 12.50, F 7.29, $H_2O$ 1.29. Found: C 49.39, H3.71, N 12.42, F 7.98, $H_2O$ 1.21 (Karl Fischer Method).

N-Phosphonooxymethyl itraconazole was prepared as trifluoroacetate salt in 32% yield by the method described for the preparation of 3 above from itraconazole (0.5 mmol) and di-tert-butyl chloromethyl phosphate 2 (2 mmol): $^1$H NMR (DMSO-d6): δ 10.44 (s, ⅔H), 10.40 (s, ⅓H), 9.33 (s, ⅔H), 9.31 (s, ⅓H), 8.33 (s, 1H), 6.8–7.7 (m, 11H), 5.91 (d, ⅔H, J=14), 5.79 (d, ⅔H, J=14), 5.08–5.18 (m, 2H), 4.37 (m, 1H), 4.10 (m, 1H), 3.93 (m, 2H), 3.76 (m, 2H), 3.34 (br.s, 4H), 3.22 (m, 4H), 1.64–1.71 (m, 2H), 1.27 (d, 3H, J=7), 0.78 (t, 3H, J=7); MS (MH$^+$=815); Anal. Calcd for $C_{36}H_{41}Cl_2N_8O_8P/1.6CF_3CO_2H/H_2O$: C 46.34, H 4.42, N 11.03, $H_2O$ 1.79. Found: C 46.03, H 4.46, N 11.08, $H_2O$ 1.64 (Karl Fischer Method).

What is claimed is:

1. A compound of the formula

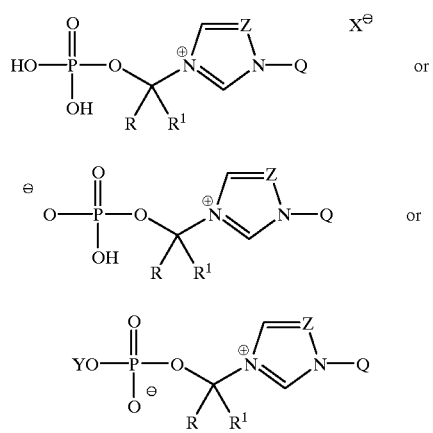

wherein R and R¹ are each independently hydrogen or $(C_1-C_6)$ alkyl, Z is nitrogen, Q is

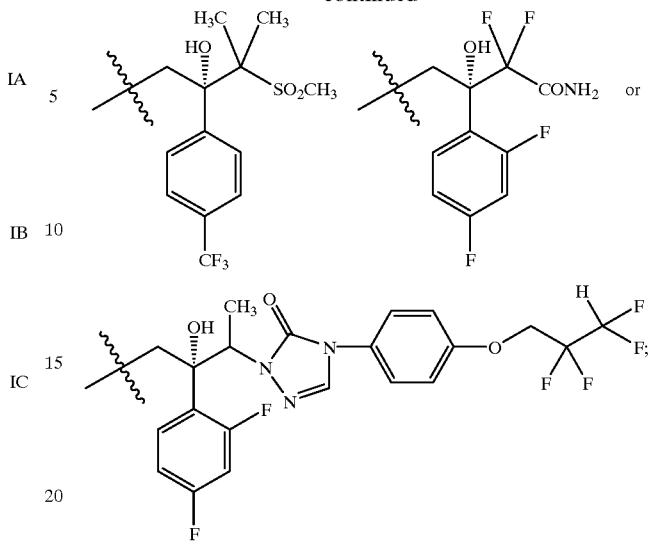

$X^{\ominus}$ is a pharmaceutically acceptable anion and Y is a pharmaceutically acceptable cation.

2. A compound of claim 1 wherein R and R¹ are both hydrogen.

3. A compound of the formula

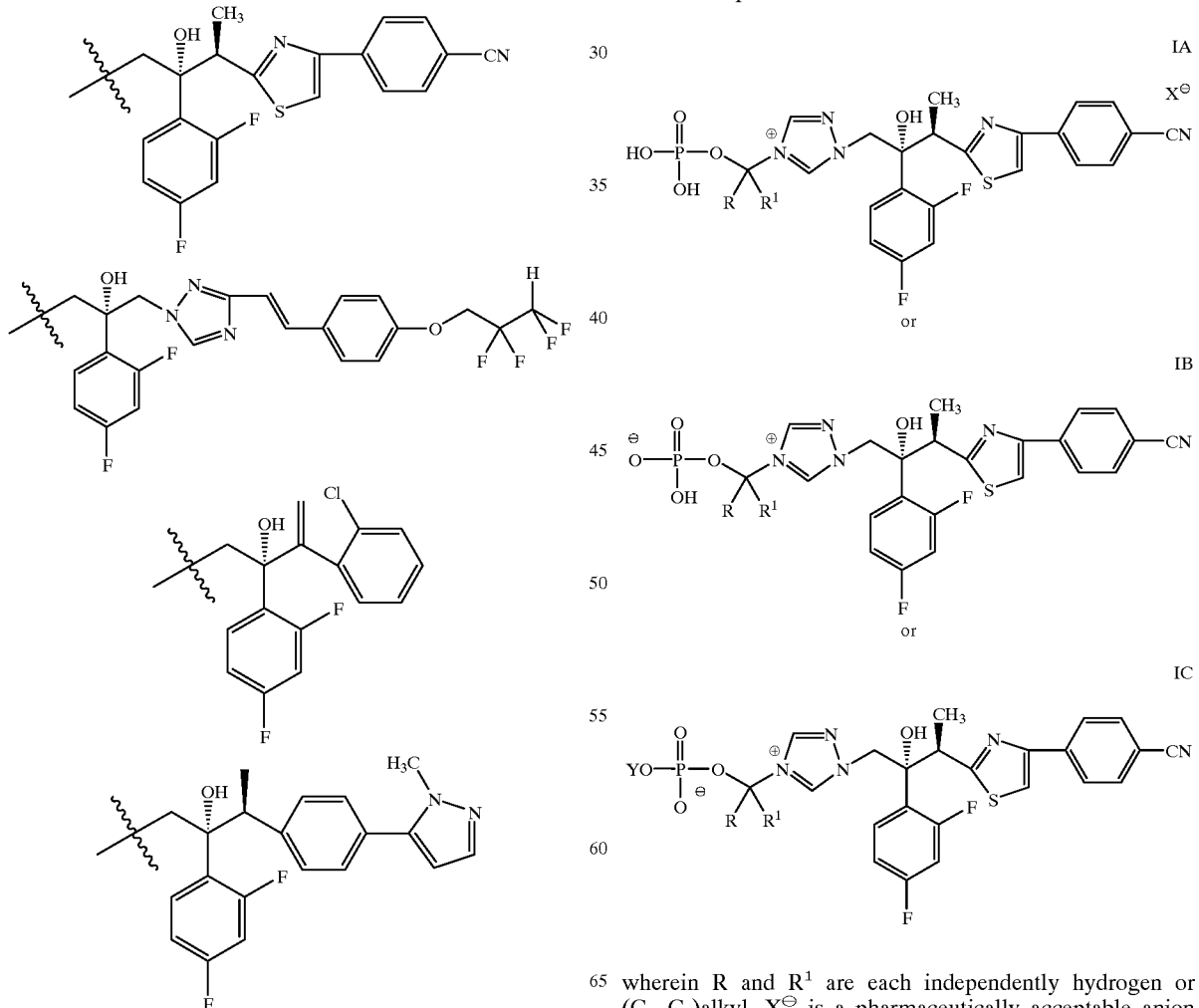

wherein R and R¹ are each independently hydrogen or $(C_1-C_6)$alkyl, $X^{\ominus}$ is a pharmaceutically acceptable anion and Y is a pharmaceutically acceptable cation.

4. The compound, (2R,3R)-3-[4-(4-cyanophenyl)thiazol-2-yl]-2-(2,4-difluorophenyl)-1-(1H,4-phosphonooxymethyl-1,2,4-triazol-1-yl)butan-2-ol, or a pharmaceutically acceptable salt thereof.

5. A method for the treatment of fungal infections, which comprises administering an effective antifungal amount of a compound of claim 1 to a mammalian host in need thereof.

6. A pharmaceutical composition comprising a compound of claim 1 in admixture with a pharmaceutically acceptable adjuvant, diluent or carrier.

* * * * *